(12) United States Patent
Homer

(10) Patent No.: US 11,357,666 B2
(45) Date of Patent: Jun. 14, 2022

(54) METHOD AND APPARATUS FOR PREDICTION OF POST-OPERATIVE PERCEIVED IRIS COLOR

(71) Applicant: Stroma Medical Corporation, Irvine, CA (US)

(72) Inventor: Gregg Homer, Irvine, CA (US)

(73) Assignee: Stroma Medical Corporation, Irvine, CA (US)

( * ) Notice: Subject to any disclaimer, the term of this patent is extended or adjusted under 35 U.S.C. 154(b) by 371 days.

(21) Appl. No.: 16/631,435

(22) PCT Filed: Aug. 16, 2017

(86) PCT No.: PCT/GB2017/052410
§ 371 (c)(1),
(2) Date: Jan. 15, 2020

(87) PCT Pub. No.: WO2018/033727
PCT Pub. Date: Feb. 22, 2018

(65) Prior Publication Data
US 2020/0206026 A1    Jul. 2, 2020

(30) Foreign Application Priority Data
Aug. 16, 2016    (WO) .................. PCT/IB2016/054907

(51) Int. Cl.
*A61F 9/008* (2006.01)
*G16H 20/40* (2018.01)
*G16H 50/20* (2018.01)

(52) U.S. Cl.
CPC ............. *A61F 9/008* (2013.01); *G16H 20/40* (2018.01); *G16H 50/20* (2018.01);
(Continued)

(58) Field of Classification Search
CPC ............... A61B 34/10; A61F 9/008; A61F 2009/00851; A61F 2009/00876; A61F 2009/00878; G16H 20/40; G16H 50/20
See application file for complete search history.

(56) References Cited

U.S. PATENT DOCUMENTS

| 6,306,127 | B2 | 10/2001 | Homer |
| 8,206,379 | B2 | 6/2012 | Homer |
| | | (Continued) | |

FOREIGN PATENT DOCUMENTS

EP    1 355 185 A2    10/2003

OTHER PUBLICATIONS

International Search Report for International Application No. PCT/GB2017/052410 dated Jan. 4, 2018.

*Primary Examiner* — Mallika D Fairchild
*Assistant Examiner* — Shreya Anjaria
(74) *Attorney, Agent, or Firm* — Perkins Coie LLP

(57) ABSTRACT

The present invention predicts prior to a laser iris color-change procedure what a patient's iris color will be after the procedure. The present invention does so by identifying and measuring a variety of anatomical features of the patient's eye that affect or are otherwise relevant to predicting the patient's post-operative iris color, translating these measurements into a post-operative iris color prediction, and communicating this prediction to the patient in a manner sufficient to manage the patient's expectations with respect to the aesthetic outcome of the procedure.

16 Claims, 2 Drawing Sheets

(52) U.S. Cl.
CPC .............. *A61F 2009/00851* (2013.01); *A61F 2009/00876* (2013.01); *A61F 2009/00878* (2013.01)

(56) References Cited

U.S. PATENT DOCUMENTS

| | | | |
|---|---|---|---|
| 2003/0007123 A1* | 1/2003 | Broderick | G02C 7/046 |
| | | | 351/159.74 |
| 2004/0073199 A1 | 4/2004 | Homer | |
| 2005/0049584 A1 | 3/2005 | Homer | |
| 2014/0148737 A1 | 5/2014 | Homer | |
| 2016/0317012 A1* | 11/2016 | Bagherinia | G06T 7/70 |

\* cited by examiner

METHOD AND APPARATUS FOR PREDICTION OF POST-OPERATIVE PERCEIVED IRIS COLOR

This application is the national phase under 35 U.S.C. § 371 as the U.S. National Phase of PCT Application No. PCT/GB2017/052410, filed Aug. 16, 2017, which is in turn a continuation-in-part of PCT Application No. PCT/IB2016/054907, filed on Aug. 16, 2016, both of which are hereby incorporated by reference in their entireties.

BACKGROUND OF THE INVENTION

The mechanisms behind iris color are surprising for at least a couple of reasons. First, under every brown iris is a blue or green iris. If the brown pigment is removed, the underlying green or blue iris is revealed. Second, a green or blue iris is not actually green or blue. Instead, the visible light entering the iris is scattered by the gray iris fibers into the light's various wavelengths (i.e., colors or, more specifically, hues). The shorter wavelengths (blue and, in some cases, green) bend and backscatter, mixing to varying degrees with the reflected light of the gray iris fibers, and creating the appearance of a blue or green iris. The longer wavelengths (red, orange, yellow, and, in some cases, green) are absorbed by the thick layer of pigment on the back of the iris (known as the Iris pigment epithelium or "IPE") before they have the opportunity to bend and backscatter. As a result, only the blue or green light is visible.

U.S. Pat. Nos. 6,306,127 and 8,206,379 disclose a procedure for altering the perceived color of a pigmented iris of a patient's eye. This procedure comprises applying electromagnetic radiation to the anterior iris surface, thereby initiating the reduction and/or elimination of the stromal pigment covering all or a portion of such surface. Once this pigment is reduced and/or eliminated, white light is able to enter the iris and backscatter to create the appearance of a blue or green iris.

Patient satisfaction is an important feature of any medical procedure. In the case of aesthetic procedures, patient satisfaction depends in large part upon the ability of the physician to manage the patient's expectations by providing the patient with a reasonably accurate prediction of the aesthetic outcome of the procedure. In the case of laser eye-color change, prediction is complicated by the occlusion of the stromal fibers by the stroma pigment. One option would be to perform the procedure on a small area of the iris behind the upper eyelid. Unfortunately, this is unlikely to provide an accurate prediction of post-operative color because a relatively large area of stromal fiber exposure is required to generate backscatter sufficient for a reasonably accurate prediction. Moreover, if any portion of the iris were treated and the patient were to decide, based upon the predicted outcome, not to proceed with the procedure, the patient would be left with a permanently discolored area on the iris (aka sectoral heterochromia).

There is therefore a need for a method and/or apparatus capable of predicting with reasonable accuracy, prior to a laser iris color-change procedure, what the patient's iris color will be after the procedure is performed and the stromal pigment has been reduced and/or eliminated.

BRIEF SUMMARY OF THE INVENTION

The present invention predicts, prior to a laser iris color-change procedure, what a patient's iris color will be after the procedure. The present invention does so by identifying and measuring a variety of anatomical features of the patient's eye that affect or are otherwise relevant to predicting the patient's post-operative iris color, deriving a post-operative iris color prediction from these measurements, and communicating this prediction to the patient in a manner sufficient to manage the patient's expectations with respect to the aesthetic outcome of the procedure. A preferred method of identifying and measuring at least some of the anatomical features of the patient's eye is to use specialized imaging and measurement devices and techniques, such as infrared iris transillumination. A preferred method of translating these measurements into a post-operative iris color prediction is to construct a database of these measurements and their associated iris colors from the relevant population pool and then compare the measurements collected from the patient with the measurements contained in the database to return a predicted iris color for the patient. Finally, a preferred method of communicating the predicted iris color to the patient is to generate an image of the patient's face, replacing the patient's pre-operative iris color with the predicted iris color (or colors, if more than one result is returned from the database search).

Other objects, features, and advantages of the present invention will become apparent upon consideration of the following detailed description and the accompanying drawings in which like reference designations represent like features throughout the figures.

DETAILED DESCRIPTION OF THE INVENTION

Figure 1:
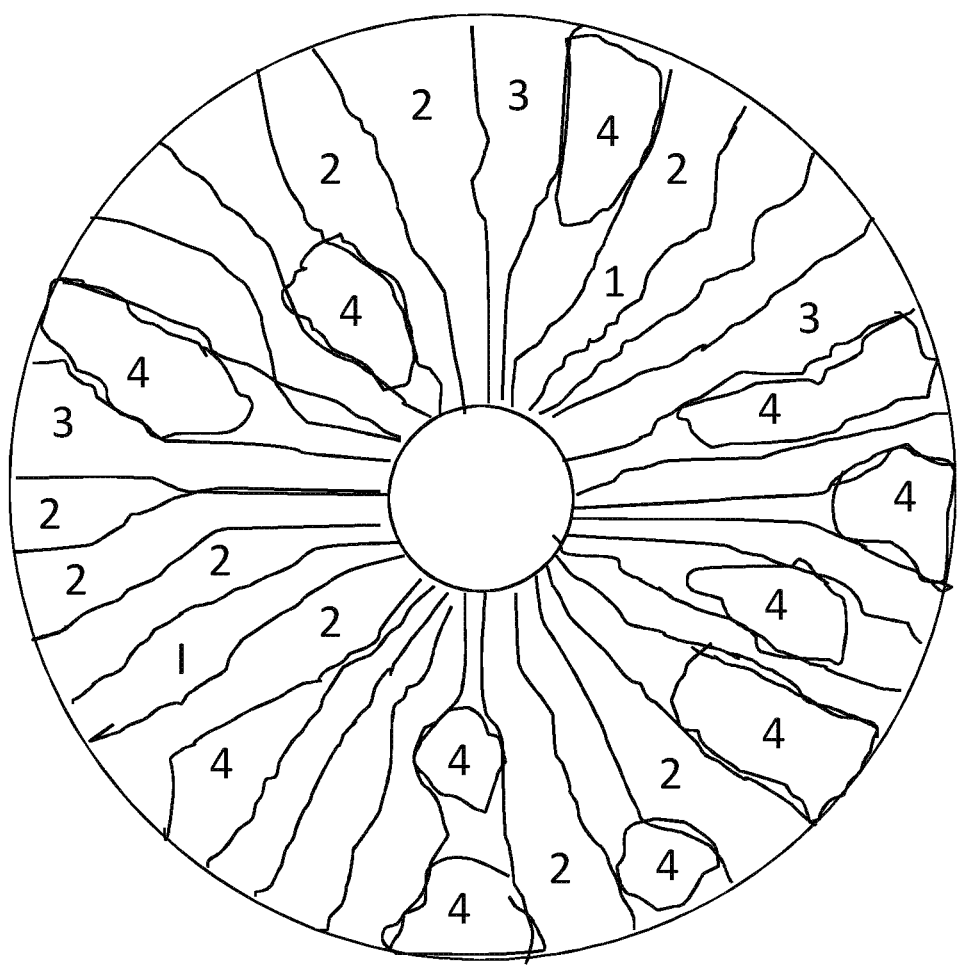
FIG. 1 shows an embodiment of a data map of a patient's perceived iris colors, featuring numbers to indicate colors.

The mechanisms behind iris color are surprising for at least a couple of reasons. First, under every brown iris is a blue or green iris. If the brown pigment is removed, the underlying green or blue iris is revealed. Second, a green or blue iris is not actually green or blue. Instead, the visible light entering the iris is scattered by the gray iris fibers into the light's various wavelengths (i.e., colors or, more specifically, hues). The shorter wavelengths (blue and, in some cases, green) bend and backscatter, mixing to varying degrees with the reflected light of the gray iris fibers, and creating the appearance of a blue or green iris. The longer wavelengths (red, orange, yellow, and, in some cases, green) are absorbed by the thick layer of pigment on the back of the iris (known as the Iris pigment epithelium or "IPE") before they have the opportunity to bend and backscatter. As a result, only the blue or green light is visible.

U.S. Pat. Nos. 6,306,127 and 8,206,379 disclose a procedure for altering the perceived color of a pigmented iris of a patient's eye. This procedure comprises applying electromagnetic radiation to the anterior iris surface, thereby initiating the reduction and/or elimination of the stromal pigment covering all or a portion of such surface. Once this pigment is reduced and/or eliminated, white light is able to enter the iris and backscatter to create the appearance of a blue or green iris.

Patient satisfaction is an important feature of any medical procedure. In the case of aesthetic procedures, patient satisfaction depends in large part upon the ability of the physician to manage the patient's expectations by providing the patient with a reasonably accurate prediction of the aesthetic outcome of the procedure. In the case of laser eye-color change, prediction is complicated by the occlusion of the stromal fibers by the stroma pigment. One option would be to perform the procedure on a small area of the iris behind the upper eyelid. Unfortunately, this is unlikely to provide an accurate prediction of post-operative color because a relatively large area of stromal fiber exposure is required to generate backscatter sufficient for a reasonably accurate prediction. Moreover, if any portion of the iris were treated and the patient were to decide, based upon the predicted outcome, not to proceed with the procedure, the patient would be left with a discolored area on the iris (aka sectoral heterochromia).

The present invention predicts, prior to a laser iris color-change procedure, what a patient's iris color will be after the procedure. The present invention does so by identifying and measuring a variety of anatomical features of the patient's eye that affect or are otherwise relevant to predicting the patient's post-operative iris color, deriving a post-operative iris color prediction from these measurements, and communicating this prediction to the patient in a manner sufficient to manage the patient's expectations with respect to the aesthetic outcome of the procedure. A preferred method of identifying and measuring at least some of the anatomical features of the patient's eye is to use specialized imaging and measurement devices and techniques, such as infrared iris transillumination. A preferred method of deriving a post-operative iris color prediction from these measurements is to compile a database of these measurements and their associated iris colors from a relevant population pool and then compare the measurements collected from the patient with the measurements contained in the database to return a predicted iris color for the patient. Finally, a preferred method of communicating the predicted iris color to the patient is to generate an image of the patient's face, replacing the patient's pre-operative iris color with the predicted iris color (or colors, if more than one result is returned from the database search).

Identifying and Measuring Anatomical Features

The invention comprises identifying and measuring a variety of anatomical features of the patient's eye that affect or are otherwise relevant to predicting the patient's post-operative iris color. A preferred method of identifying and measuring at least some of the anatomical features of the patient's eye is to use specialized imaging and measurement devices and techniques. Following are examples of some of these anatomical features and some of the devices and techniques suitable for identifying and measuring these features:

Iris Stroma—Thickness

Color comprises hue, saturation, and value. Hue can be defined as the attribute of a color by which it is discernible as a primary color or some combination thereof, dependent upon its dominant wavelength(s), and independent of its or their saturation or value. Saturation can be defined as the intensity of a color, expressed as the degree to which it differs from white. Value can be defined as the brightness of color, defined by the amount of light it emits. In this respect, value may be thought of the inverse of saturation insofar as the more a color differs from white, the less light it will reflect, and vice versa.

The thickness of the iris stroma refers to the distance from its anterior surface to its posterior surface, without regard to the anterior and posterior iris pigment layers. Iris stroma thickness is relevant to predicting its post-operative hue. As explained above, the post-operative iris stroma scatters incoming visible light into its component wavelengths, each representing a different hue, and the longer wavelengths are absorbed by the IPE, while the shorter wavelengths backscatter anteriorly. The distance from the stroma fibers to the IPE is therefore relevant to predicting post-operative hue. When this distance is shorter, the IPE is more likely to absorb those wavelengths longer than blue, thereby creating a blue iris. Where this distance is longer, the IPE is more likely to absorb those wavelengths longer than blue and green, thereby creating a green iris.

Iris thickness may vary widely from the pupil to the limbus, depending upon the dilation or constriction of the pupil. When a pupil dilates, the iris folds like an opening curtain, increasing variations in iris thickness. When a pupil constricts, the iris unfolds like a closing curtain, reducing variations in iris thickness. The pupil can be constricted by a variety of methods, including bright light and various medications, such as topical cholinergic agonists like Pilocarpine. The thickness of a non-constricted iris may be determined at its thinnest point or at various locations. It can also be measured using the Zhongshan Angle Assessment Program, which measures iris thickness at 750 µm and 2000 µm from the scleral spurs and the maximum iris thickness at the middle one third of the iris. Alternatively, the iris may be constricted prior to measurement.

Iris thickness may, in embodiments of the invention, be imaged and measured using any number of devices and techniques, including optical coherence tomography or "OCT," anterior segment optical coherence tomography or "ASOCT," spectral domain optical coherence tomography or "SDOCT," and ultrasound biomicroscopy or "UBM."

Melanocytes and Lipofuscin—Location, Density, Color, and Thickness

There are generally two sources of pigment in the human eye: melanocytes and lipofuscin. Melanocytes are cells that produce pigmented granules of melanin called "melanosomes." Melanosomes can be brown (called "eumelanin") or yellow (called "pheomelanin"). Lipofuscin is a pigmented, insoluble granule, typically yellowish brown in color, comprised of protein and lipid, that accumulates in cells as part of the normal aging process or as the result of disease. Some commentators have identified lipofuscin as the waste product of oxidative metabolism, stored within each cell of the body and accumulated over time.

The location, density, color, and thickness of these pigments can influence post-operative iris color. Both types of pigment reside throughout the eye, but those most influencing post-operative iris color reside inside the iris stroma. When the anterior stromal pigment is removed from the iris, and the blue or green light is backscattered, pigments residing within the iris stroma can absorb this blue or green light, thereby diminishing the blue or green backscatter and permitting the gray light reflected by the stroma fibers to appear more prominently, resulting in a gray-blue or gray-green iris.

The greater the density of the pigments residing within the iris stroma, the greater the absorption of the blue or green backscatter, and the greater the appearance of the gray fibers. In terms of color prediction, the greater the density of these intra-stromal pigments, the lower the saturation and the higher the value.

The color of these intra-stromal pigments can also have a significant effect on the post-operative iris color. The darker the pigments, the more they absorb the backscattered light, allowing more of the gray of the stromal fibers to show, thereby reducing saturation and increasing value. The lighter the pigments, the less they absorb the backscattered light, and the backscattered light overpowers the gray of the stromal fibers, thereby increasing saturation and reducing value These pigments, particularly lipofuscin, can also reside in the aqueous humor of the anterior segment and can coat and color the corneal endothelium. Again, depending upon the density and color of these pigments, they can affect the perceived iris color. If the pigments are denser and/or darker, they will absorb more of both the backscattered light and the grey of the stromal fibers, resulting in a post-operative iris that is dull in hue, low in saturation, and low in value. If the pigments are less dense and/or lighter, they can also affect the hue of the post-operative iris, such as making a blue iris appear green or making a green iris appear more yellow-green.

Finally, the color, density, and thickness of the IPE can influence the post-operative iris color. The darker, denser, and/or thicker the IPE, the more pronounced the limbal ring (which results from the IPE showing through the thin iris tissue at the limbus). In addition, the darker, denser, and/or thicker the IPE, the greater the absorption of the longer wavelengths, thereby affecting iris hue.

Pigment color, and/or density, and/or thickness may, in embodiments of the invention, be imaged and measured using any number of devices and techniques, including optical coherence tomography or "OCT," anterior segment optical coherence tomography or "ASOCT," spectral domain optical coherence tomography or "SDOCT," and ultrasound biomicroscopy or "UBM." In the case of pigments coating or coloring the corneal endothelium and/or residing in the aqueous humor of the anterior chamber, such devices and techniques also include a slit lamp or penlight examination of the anterior chamber.

Iris Stroma Fibers—Physical Dimensions

The stroma fibers are responsible for the scattering, bending, and backscattering of the visible light entering the iris post-operatively. Accordingly, the physical dimensions of these fibers are relevant to the prediction of the patient's post-operative iris color. These dimensions include the thickness, density, axial periodicity, depth, and arrangement of these fibers. By way of example, the thicker and/or denser the stromal fibers, the more gray light they reflect, and the more they occlude and/or absorb the backscattered light.

The physical dimensions of the iris stroma fibers may, in embodiments of the invention, be imaged and measured using any number of devices and techniques, including optical coherence tomography or "OCT," anterior segment optical coherence tomography or "ASOCT," spectral domain optical coherence tomography or "SDOCT," ultrasound biomicroscopy or "UBM," and iris transillumination (using infrared or visible light).

Stromal Vasculature—Physical Dimensions

The stroma vasculature runs throughout the iris stroma, and the physical dimensions of these vessels can influence the scattering, bending, and backscattering of the visible light entering the iris post-operatively. Accordingly, the physical dimensions of these vessels are relevant to the prediction of the patient's post-operative iris color. These dimensions include the thickness, density, axial periodicity, depth, and arrangement of these vessels. By way of example, the thicker and/or denser these vessels, the more they occlude and/or absorb the backscattered light.

The physical dimensions of the stromal vasculature may, in embodiments of the invention, be imaged and measured using any number of devices and techniques, including optical coherence tomography or "OCT," anterior segment optical coherence tomography or "ASOCT," spectral domain optical coherence tomography or "SDOCT," ultrasound biomicroscopy or "UBM," and iris transillumination (using infrared or visible light).

Anterior Chamber—Depth

The depth of the anterior chamber of the eye may vary significantly from patient to patient. It generally varies between 1.5 and 4.0 mm and averages 3.0 mm. The deeper the anterior chamber, the greater the potential volume of pigment in the aqueous humor of the anterior chamber, thereby potentially increasing the pigment effects described above. Accordingly, anterior chamber depth may be relevant to the prediction of the patient's post-operative iris color.

There are various methods of measuring anterior chamber depth, which may be used in embodiments of the invention, including a slit lamp examination (using, for example, the Van Herick or Smith method), optical coherence tomography or "OCT," anterior segment optical coherence tomography or "ASOCT," spectral domain optical coherence tomography or "SDOCT," ultrasound biomicroscopy or "UBM," the penlight method, the Orbscan topograph system (Bausch & Lomb Surgical Inc., Rancho Cucamonga, Calif., USA), the IOLMaster (Carl Zeiss Meditec, Jena, Germany), ultrasound (e.g., A-Scan, Alcon, Fort Worth, Tex., USA), Scheimpflug photography (e.g., Pantacam, (Oculus, Wetzlar, Germany), and smartphone photography using the "EZ ratio."

Cornea—Curvature and Clarity

The curvature and clarity of the cornea are also relevant to the prediction of post-operative iris color. The corneal curvature may be associated with the anterior chamber depth, thereby influencing color as described above. The corneal curvature also refracts the light entering and exiting the iris stroma, thereby altering the light's path and potentially affecting the perceived iris color. Finally, the clarity of the cornea may influence the saturation and value of the perceived iris color by limiting or permitting transmittance.

There are various methods of measuring corneal curvature, which may be used in embodiments of the invention, including the manual keratometer (e.g., Rodenstock, Munchen-Hamburg, Germany), the Galilei Dual-Scheimpflug analyzer (Ziemer Group, Port, Switzerland), the corneal topographer (e.g., Tomey TMS-1, Tomey, Phoenix, Ariz., USA), the automated IOLMaster keratometer (Carl Zeiss GmbH, Oberkochen, Germany), optical coherence tomography or "OCT," anterior segment optical coherence tomography or "ASOCT," spectral domain optical coherence tomography or "SDOCT," ultrasound biomicroscopy or "UBM," the Orbscan topograph system (Bausch & Lomb Surgical Inc., Rancho Cucamonga, Calif., USA), the IOLMaster (Carl Zeiss Meditec, Jena, Germany), ultrasound (e.g., A-Scan, Alcon, Fort Worth, Tex., USA), and Scheimpflug photography (e.g., Pantacam, (Oculus, Wetzlar, Germany).

Corneal clarity may, in embodiments of the invention, be measured using digital imaging or corneal densitometry (e.g., Pentacam Scheimpflug device, Oculus Optikgёrate GmbH, Wetzlar, Germany.

Iris—Curvature

Iris curvature is relevant to predicting post-operative iris color because the curvature of the iris can influence the backscatter of the iris stromal fibers. Iris curvature may, in embodiments of the invention, be imaged and/or measured using any number of devices and techniques, including optical coherence tomography or "OCT," anterior segment optical coherence tomography or "ASOCT," spectral domain optical coherence tomography or "SDOCT," and ultrasound biomicroscopy or "UBM."

Deriving Color Prediction from Measurements

Once the anatomical features of the patient's eye relevant to predicting the patient's post-operative iris color have been identified and measured, a reasonably accurate prediction must be derived therefrom. A preferred method of deriving a post-operative iris color prediction from these measurements is to compile a database of these measurements and their associated iris colors from a relevant population pool and then compare the measurements collected from the patient with the measurements contained in the database to return a predicted iris color for the patient.

The database may comprise any combination of text, images, and/or other data. It may include a database management system or "DBMS," may comprise data in digital and/or analog form, may store and/or be located locally or remotely to one or more of the remaining components of the present invention, may comprise one or more relational databases, operational databases, database warehouses, distributed databases, and/or end-user databases, may or may not be electronic, and may or may not be networked. In the case of a computer database, the data may reside in volatile memory and/or non-volatile memory.

The comparison of the measurements collected from the patient with the measurements contained in the database may be accomplished using a data-processing device. The data-processing device is capable producing a defined set of outputs for a given set of inputs. It may operate mechanically and/or electronically, and its processing function may comprise data format conversion, data verification, data validation, data sorting, data summarization, data aggregation, data analysis, and/or data reporting. Examples of data-processing devices include computers, calculators, central processing units (CPU), and graphical processing units (GPU).

Figure 2:
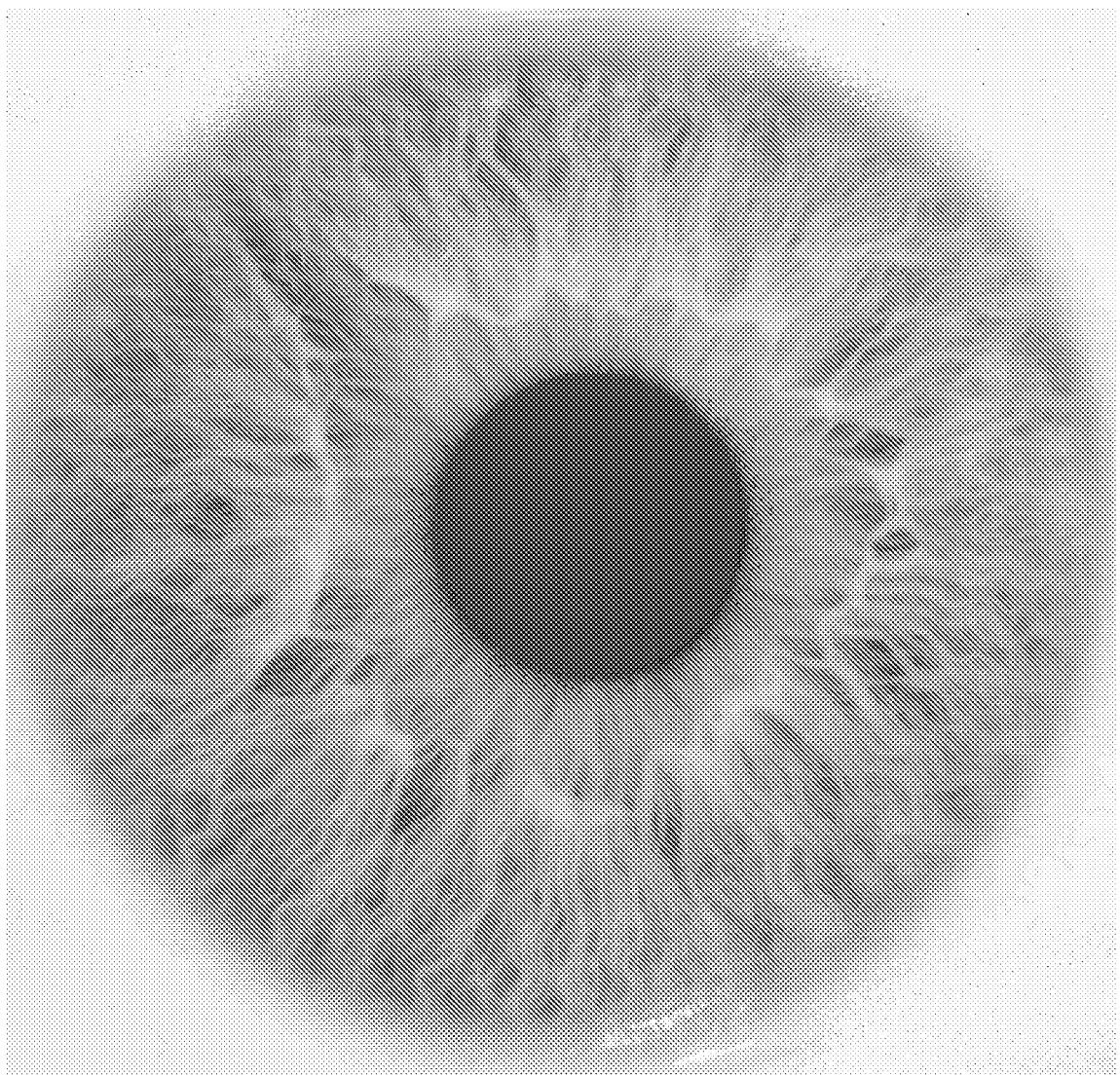
FIG. 2 shows an embodiment of a visual map of a patient's iris colors. Note that FIG. 2 is a gray scale image, so it only approximates the true color variations of the embodiment.

In one embodiment, the anatomical features of the patient's eye relevant to predicting the patient's post-operative iris color are identified and measured. A database has been compiled comprising measurements of anatomical features relevant to iris color and images and/or other data concerning the iris colors associated with each such measurement. In a sub-embodiment, this database is a relational database, in which the images and/or data are arranged in a lookup table, one axis of which (i.e., either the rows or the columns) comprises ranges of measurements, and the other axis of which comprises images and/or other data concerning the iris colors associated with each such range. A data-processing device then searches the database for images and/or data relevant to the anatomical features of the patient's eye. In a sub-embodiment, the search is conducted in Structured Query Language or "SQL," such that each data point of the patient measurements is associated with its range within the database lookup table, and a data map of iris color categories is returned. See FIG. 1 for an exemplary data map of a patient's perceived iris colors. This data map is then converted to a visual map, wherein an animated iris image is generated, which iris image comprises each of the perceived iris color categories of the patient iris, arranged as they appear in the patient's iris stroma. See FIG. 2 for an exemplary visual map of a patient's perceived iris color categories.

In another embodiment, the data and/or images of one or more patients are stored in the database. In a sub-embodiment, pre-operative and post-operative data and/or images of the same patients are captured and compared to the predicted post-op color maps (data and/or visual maps).

Where the pre-operative predictions and post-operative data and/or images of a given patient are consistent (as defined by a predetermined differential tolerance), no changes are made to the database and/or data-processing methodologies. Where the pre-operative predictions and post-operative data and/or images of a given patient are not consistent, however, the database and/or data-processing methodologies are modified to improve the accuracy of iris color predictions. By way of example, the ranges for a given data point under a given iris color category might be modified. In yet another embodiment, pre-operative and post-operative data and/or images of the same patients are captured and stored in the database in order to add more data points to the database, thereby improving its predictive power.

Communicating Prediction to Patient

Once the anatomical features of the patient's eye relevant to predicting the patient's post-operative iris color have been identified and measured, a database is queried, and a reasonably accurate prediction is derived therefrom, the prediction must be communicated to the patient. In one embodiment, the prediction comprises a verbal or written communication describing the range of possible iris colors. In another embodiment, the prediction comprises an image or series of images, featuring one or more post-operative iris color predictions. In yet another embodiment, the prediction comprises an image or series of images of the patient's face, with his or her irides replaced with images of one or more post-operative iris color predictions.

In one embodiment, a display device is used to present the post-operative iris color predictions to the patient. The display device comprises any device that is capable of displaying images and/or other data in a format susceptible to human interpretation. The image and/or other data may appear in two- or three-dimensional form. Examples of display devices include photographs (digital and analog), digital files (e.g., .jpg, .jpeg, .tif, .tiff, .png, .pdf, .bmp, and .gif), digital image print-outs, cathode ray tube displays, light-emitting diode displays, electroluminescent displays, electronic paper, plasma display panels, liquid crystal displays, high-performance addressing displays, thin-film transistor displays, organic light-emitting diode displays, surface-conduction electron-emitter displays, field emission displays, laser TVs, carbon nanotubes, quantum dot displays, interferometric modulator displays, digital microshutter displays, swept-volume displays, varifocal mirror displays, emissive volume displays, laser displays, holographic displays, or light field displays.

This disclosure of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the claims contained in this Application, as amended.

I claim:

1. A method for generating predictions, at a time prior to a laser iris color-change procedure, of what patients' iris color will be after the procedure is performed and its effects are realized, characterized in that the method comprises:

measuring anatomical features of a patient's eye, wherein measuring the anatomical features of a patient's eye comprises measuring a thickness, density, axial periodicity, depth, or arrangement of iris stroma fibers using infrared light during iris transillumination;

generating search criteria based on measurements of the anatomical features of the patient's eye;

querying a database comprising measurements of the anatomical features of a population of eyes and iris colors associated with the anatomical features of the population of eyes using the search criteria by comparing the search criteria with the measurements of the anatomical features of the population of eyes and iris colors associated with the anatomical features of the population of eyes contained in the database;

generating a prediction of iris color-change based on a reduction or elimination of stromal pigment; and generating for display, on a display device, at least one of a description or image of the prediction.

2. The method according to claim 1, wherein the anatomical features of the patient's eye further comprise at least one of: a location, density, color, or thickness of at least one of melanocytes or lipofuscin; a thickness, density, axial periodicity, depth, or arrangement of iris vasculature; anterior chamber depth; or a corneal curvature or clarity.

3. The method according to claim 1, wherein measuring the anatomical features of the patient's eye further comprises performing optical coherence tomography, spectral domain optical coherence tomography, or ultrasound biomicroscopy.

4. The method according to claim 1, wherein the anatomical features of the patient's eye comprise a thickness of a non-constricted iris, and wherein measuring the anatomical features of the patient's eye relevant to the prediction further comprises performing optical coherence tomography, anterior segment optical coherence tomography, spectral domain optical coherence tomography, or ultrasound biomicroscopy.

5. The method according to claim 1, wherein the anatomical features of the patient's eye comprise an iris curvature, and wherein measuring the anatomical features of the patient's eye relevant to the prediction further comprises performing optical coherence tomography, anterior segment optical coherence tomography, spectral domain optical coherence tomography, or ultrasound biomicroscopy.

6. The method according to claim 1, wherein displaying at least one of a description or image of the prediction further comprises:

generating a data map of a patient's iris colors; and converting the data map to a visual map may featuring an animated iris image.

7. The method according to claim 1, wherein generating the prediction further comprises modifying ranges for a given data point under a given iris color category.

8. A method for generating predictions, at a time prior to a laser iris color-change procedure, of what patients' iris color will be after the procedure is performed and its effects are realized, characterized in that the method comprises:

measuring anatomical features of a patient's eye, wherein measuring the anatomical features of a patient's eye comprises measuring an iris stroma thickness by determining a distance from a stroma fiber in the patient's eye to an iris pigment epithelium in the patient's eye;

generating search criteria based on measurements of the anatomical features of the patient's eye;

querying a database comprising measurements of the anatomical features of a population of eyes and iris colors associated with the anatomical features of the population of eyes using the search criteria;

generating a prediction of iris color-change based on a reduction or elimination of stromal pigment by comparing the search criteria with the measurements of the anatomical features of the population of eyes and iris colors associated with the anatomical features of the population of eyes contained in the database; and generating for display, on a display device, at least one of a description or image of the prediction.

9. The method according to claim 8, wherein the anatomical features of the patient's eye comprise a thickness of a non-constricted iris, and wherein measuring the anatomical features of the patient's eye relevant to the prediction further comprises performing optical coherence tomography, anterior segment optical coherence tomography, spectral domain optical coherence tomography, or ultrasound biomicroscopy.

10. The method according to claim 8, wherein the anatomical features of the patient's eye comprise location, density, color, or thickness of at least one of melanocytes or lipofuscin, and wherein measuring the anatomical features of the patient's eye relevant to the prediction further comprises performing optical coherence tomography, anterior segment optical coherence tomography, spectral domain optical coherence tomography, or ultrasound biomicroscopy.

11. The method according to claim 8, wherein the anatomical features of the patient's eye comprise a thickness, density, axial periodicity, depth, or arrangement of iris stroma fibers, and wherein measuring the anatomical features of the patient's eye relevant to the prediction further comprises performing optical coherence tomography, anterior segment optical coherence tomography, spectral domain optical coherence tomography, or ultrasound biomicroscopy.

12. The method according to claim 8, wherein the anatomical features of the patient's eye comprise a thickness, density, axial periodicity, depth, or arrangement of iris vasculature, and wherein measuring the anatomical features of the patient's eye relevant to the prediction further comprises performing optical coherence tomography, anterior segment optical coherence tomography, spectral domain optical coherence tomography, or ultrasound biomicroscopy.

13. The method according to claim 8, wherein the anatomical features of the patient's eye comprise a corneal curvature or clarity, and wherein measuring the anatomical features of the patient's eye relevant to the prediction further comprises performing corneal densitometry.

14. The method according to claim 8, wherein displaying at least one of a description or image of the prediction further comprises:

generating a data map of a patient's iris colors; and converting the data map to a visual map featuring an animated iris image.

15. The method according to claim 8, wherein generating the prediction further comprises modifying ranges for a given data point under a given iris color category.

16. A method for generating predictions, at a time prior to a laser iris color-change procedure, of what patients' iris color will be after the procedure is performed and its effects are realized, characterized in that the method comprises:

measuring anatomical features of a patient's eye, wherein the anatomical features of the patient's eye comprise a corneal curvature or clarity, and wherein measuring the anatomical features of the patient's eye relevant to the prediction further comprises performing corneal densitometry;

generating search criteria based on measurements of the anatomical features of the patient's eye;

querying a database comprising measurements of the anatomical features of a population of eyes and iris colors associated with the anatomical features of the population of eyes using the search criteria;

generating a prediction of iris color-change based on a reduction or elimination of stromal pigment by comparing the search criteria with the measurements of the anatomical features of the population of eyes and iris colors associated with the anatomical features of the population of eyes contained in the database; and generating for display, on a display device, at least one of a description or image of the prediction.

* * * * *